(12) United States Patent
Chong et al.

(10) Patent No.: US 9,895,356 B2
(45) Date of Patent: Feb. 20, 2018

(54) METHODS AND COMPOSITIONS FOR TREATING ANXIETY

(71) Applicant: HYDRA BIOSCIENCES, INC., Cambridge, MA (US)

(72) Inventors: Jayhong A. Chong, Brookline, MA (US); Christopher Fanger, Bolton, MA (US); Magdalene M. Moran, Brookline, MA (US); Elisha Singer, Philadelphia, PA (US); Timothy Strassmaier, Watertown, MA (US); Howard Ng, Summit, NJ (US)

(73) Assignee: Hydra Biosciences, Inc., Cambridge, MA (US)

( * ) Notice: Subject to any disclaimer, the term of this patent is extended or adjusted under 35 U.S.C. 154(b) by 0 days.

(21) Appl. No.: 14/837,717

(22) Filed: Aug. 27, 2015

(65) Prior Publication Data

US 2016/0220539 A1  Aug. 4, 2016

Related U.S. Application Data

(63) Continuation of application No. 14/102,020, filed on Dec. 10, 2013, now Pat. No. 9,139,573, which is a continuation of application No. 13/057,527, filed as application No. PCT/US2009/052971 on Aug. 6, 2009, now Pat. No. 8,633,233.

(60) Provisional application No. 61/086,784, filed on Aug. 6, 2008, provisional application No. 61/086,785, filed on Aug. 6, 2008, provisional application No. 61/086,787, filed on Aug. 6, 2008.

(51) Int. Cl.
| | |
|---|---|
| *A61K 31/423* | (2006.01) |
| *A61K 31/00* | (2006.01) |
| *A61K 31/164* | (2006.01) |
| *A61K 31/4184* | (2006.01) |
| *A61K 31/53* | (2006.01) |
| *C07D 235/30* | (2006.01) |
| *C07D 251/16* | (2006.01) |
| *C07D 251/46* | (2006.01) |
| *C07D 251/52* | (2006.01) |
| *C07D 263/58* | (2006.01) |
| *C07D 405/14* | (2006.01) |
| *C07D 409/06* | (2006.01) |
| *C07D 409/12* | (2006.01) |
| *A61K 31/4196* | (2006.01) |

(52) U.S. Cl.
CPC ............ *A61K 31/423* (2013.01); *A61K 31/00* (2013.01); *A61K 31/164* (2013.01); *A61K 31/4184* (2013.01); *A61K 31/4196* (2013.01); *A61K 31/53* (2013.01); *C07D 235/30* (2013.01); *C07D 251/16* (2013.01); *C07D 251/46* (2013.01); *C07D 251/52* (2013.01); *C07D 263/58* (2013.01); *C07D 405/14* (2013.01); *C07D 409/06* (2013.01); *C07D 409/12* (2013.01)

(58) Field of Classification Search
CPC .. A61K 31/423; A61K 31/4196; A61K 31/00; A61K 31/164; A61K 31/4184; A61K 31/53
See application file for complete search history.

(56) References Cited

U.S. PATENT DOCUMENTS

| | | | |
|---|---|---|---|
| 6,825,223 B2 | 11/2004 | Shibuya et al. | |
| 6,919,339 B2 | 7/2005 | Campbell et al. | |
| 7,868,028 B2 | 1/2011 | Drasner et al. | |
| 2005/0182011 A1 | 8/2005 | Olson et al. | |
| 2007/0232673 A1 | 10/2007 | Roth et al. | |
| 2014/0249173 A1* | 9/2014 | Coric | A61K 31/13 514/289 |

FOREIGN PATENT DOCUMENTS

WO  2006089168 A2  8/2006

OTHER PUBLICATIONS

Bahnasi et al. "Modulation of TRPC5 cation channels by halothane, chloroform and propofol", British Journal of Pharmacology (2008) vol. 153, No. 7, pp. 1505-1512.

International Search Report and Written Opinion for PCT/US2009/052971 dated Mar. 15, 2010.

Mizota et al. "Endocrine Disrupting Chemical Atrazine Causes Degranulation through Gq/11 Protein-Coupled Neurosteroid Receptor in Mast Cells" Toxicological Sciences 90(2) pp. 362-368.

* cited by examiner

*Primary Examiner* — Jennifer M Kim
(74) *Attorney, Agent, or Firm* — Goodwin Procter LLP

(57) ABSTRACT

Methods of treating a TRPC5 mediated disorder in a subject by administering an effective amount of a TRPC5 antagonist, such as a compound disclosed herein, are described.

17 Claims, No Drawings

METHODS AND COMPOSITIONS FOR TREATING ANXIETY

CROSS REFERENCE TO RELATED APPLICATIONS

This application is a continuation of U.S. patent application Ser. No. 14/102,020, filed Dec. 20, 2013, which is a continuation of U.S. Pat. No. 8,633,233, filed Sep. 15, 2011, which is a national stage application under 35 U.S.C. § 371 of International Application No. PCT/US2009/052971, filed Aug. 6, 2009, which claims priority from U.S. Provisional Applications 61/086,784, 61/086,785, and 61/086,787, all of which were filed Aug. 6, 2008. Each of these patents and patent applications are hereby incorporated by reference in its entirety.

BACKGROUND

A variety of ion channel proteins exist to mediate ion flux across cellular membranes. The proper expression and function of ion channel proteins is essential for the maintenance of cell function, intracellular communication, and the like. Numerous diseases are the result of misregulation of membrane potential or aberrant calcium handling. Given the central importance of ion channels in modulating membrane potential and ion flux in cells, identification of agents that can promote or inhibit particular ion channels are of great interest as potential therapeutic agents.

SUMMARY OF THE INVENTION

The present invention provides methods and compositions for treating conditions such as pain and/or anxiety by modulating the activity of the transient receptor potential cation channel subfamily C, member 5 (TRPC5), which can exist in homomultimeric form as well as heteromultimeric form with other ion channels such as TRPC1 or TRPC3 (i.e., TRPC5-TRPC1 and TRPC1-TRPC3-TRPC5). The compounds described herein modulate the function of TRPC5 by inhibiting a TRPC5-mediated ion flux or by inhibiting the inward current, the outward current, or both currents mediated by TRPC5. The inhibition of a particular current is the ability to inhibit or reduce such current (e.g., inward and/or outward) in an in vitro or an in vivo assay. The activation of a particular current is the ability to activate or increase such current (e.g., inward and/or outward) in an in vitro or an in vivo assay.

In one aspect, the invention relates to a method for treating a condition for which reduced TRPC5 activity can reduce the severity of the condition, by administering a TRPC5 antagonist that inhibits TRPC5-mediated current and/or TRPC5-mediated ion flux. Described in greater detail below are TRPC5 antagonists that have measured $IC_{50}$'s for inhibition of TRPC5 of 10 micromolar or less, 5 micromolar or less, 2 micromolar or less, 1 micromolar or less, 500 nanomolar or less, 200 nanomolar or less, 100 nanomolar or less, or 10 nanomolar or less. In certain embodiments, a TRPC5 antagonist inhibits one or both of inward and outward TRPC5-mediated currents with an $IC_{50}$ of 1 micromolar or less, and more preferably with an $IC_{50}$ of 500 nanomolar or less, 200 nanomolar or less, 100 nanomolar or less, 25 nanomolar or less, or 10 nanomolar or less. In certain embodiments, the TRPC5 antagonist inhibits at least 95% of TRPC5-mediated current or TRPC5-mediated ion flux when administered at 5 micromolar or less, and more preferably when administered at 1 micromolar or less.

In another aspect, a TRPC5 antagonist such as a compound described herein can be used to inhibit a function of TRPC5, for example a TRPC5-mediated current and/or a TRPC5-mediated ion flux. In some embodiments, a TRPC5 antagonist can be used to inhibit a TRPC5 mediated current in vitro, for example in cells in culture. In other embodiments, a TRPC5 antagonist such as a compound described herein can be used to inhibit a TRPC5 mediated current in vivo. In certain embodiments, a TRPC5 antagonist such as a compound described herein inhibits both an inward and an outward TRPC5-mediated current.

In one aspect, the invention features a method of treating a TRPC5 mediated disorder by administering an effective amount of a compound of formula (I), or a pharmaceutically acceptable salt thereof:

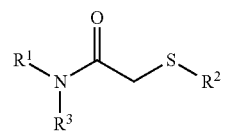

Formula (I)

wherein
$R^1$ is aryl or heteroaryl, optionally substituted with 1-5 $R^4$;
$R^2$ is heteroaryl, optionally substituted with 1-5 $R^5$;
$R^3$ is H, $C_1$-$C_6$ alkyl, arylalkyl, or a nitrogen protecting group;
each $R^4$ is independently $C_1$-$C_6$ alkyl, $C_1$-$C_6$ haloalkyl, —C(O)$R^6$; —C(O)O$R^6$, O$R^6$, —C(O)N$R^7R^8$, or 2 $R^4$, taken together with the carbon to which they are attached, form a 4-6 membered ring;
each $R^5$ is independently alkyl, cyclyl, heterocyclyl, aryl, or heteroaryl;
each $R^6$ is independently H, $C_1$-$C_6$ alkyl, or $C_1$-$C_6$ haloalkyl; and
each $R^7$ and $R^8$ is independently H or $C_1$-$C_6$ alkyl.

In some embodiments, $R^1$ is aryl, e.g., phenyl. In some embodiments, $R^1$ is substituted by 1 $R^4$. In some embodiments, $R^4$ is $C_1$-$C_6$ haloalkyl. In some embodiments, $R^4$ is $CF^3$. In some embodiments, $R^1$ is substituted by 2 $R^4$, for example, wherein $R^1$ is

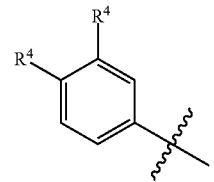

In some embodiments, $R^1$ is

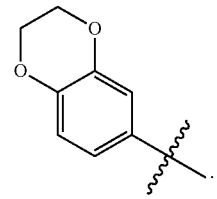 [SMILES: *c1ccc2c(c1)OCCO2]

In some embodiments, $R^1$ is heteroaryl.

In some embodiments, $R^2$ is a 5 membered heteroaryl, for example, $R^2$ is tetrazolyl. In some embodiments, $R^2$ is unsubstituted. In some embodiments, $R^2$ is substituted by 2 $R^5$. In some embodiments, $R^2$ is

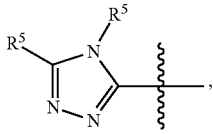

wherein each $R^5$ is independently alkyl or heteroaryl. In some embodiments, $R^2$ is

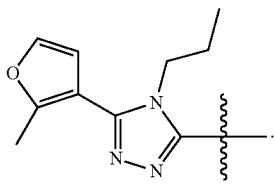 [SMILES: *c1nnc(-c2ccoc2C)n1CCC]

In some embodiments, $R^2$ is a fused heteroaryl, for example, a 2-ring fused heteroaryl. In some embodiments, $R^2$ is

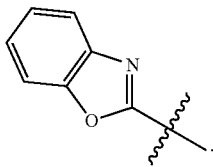 [SMILES: *c1nc2ccccc2o1]

In some embodiments, $R^3$ is H.

Exemplary compounds of formula (I) include those described in Table 1.

In another aspect, the invention features a method for treating a TRPC5 mediated disorder by administering an effective amount of a compound of formula (II), or a pharmaceutically acceptable salt thereof:

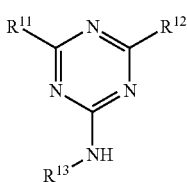

Formula (II)

wherein $R^{11}$ is halo, $C_1$-$C_6$ alkoxy, cycyl, heterocyclyl, aryl, or heteroaryl; optionally substituted with 1-3 $R^{16}$;

$R^{12}$ is $OR^{17}$, $SR^{17}$, or $NR^{14}R^{15}$;

$R^{13}$ is H, cycyl, heterocyclyl, aryl, or heteroaryl; optionally substituted with 1-3 $R^{18}$;

each $R^{14}$ and $R^{15}$ is independently H or $C_1$-$C_6$ alkyl optionally substituted with 1-3 $R^{19}$;

each $R^{16}$ and $R^{18}$ is independently $C_1$-$C_6$ alkyl or $C_1$-$C_6$ haloalkyl;

$R^{17}$ is $C_1$-$C_6$ alkyl, optionally substituted with 1-3 $R^{19}$;

$R^{19}$ is $C(O)OC_1$-$C_6$alkyl, $C(O)C_1$-$C_6$alkyl, or $OC(O)C_1$-$C_6$alkyl.

In some embodiments, $R^{11}$ is cyclyl, heterocyclyl, aryl, heteroaryl, or $NR^{14}R^{15}$; optionally substituted with 1-3 $R^{16}$. In some embodiments, $R^{11}$ is cyclyl, e.g., a bridged cyclyl such as adamantyl. In some embodiments, $R^{11}$ is heteroaryl, for example, a nitrogen containing heteroaryl. In some embodiments, $R^{11}$ is aryl, e.g., phenyl. In some embodiments, phenyl is substituted by 1 $R^{16}$. In some embodiments, $R^{16}$ is haloalkyl. In some embodiments, $R^{11}$ is $C_1$-$C_6$ alkoxy.

In some embodiments, $R^{12}$ is $OR^{17}$. In some embodiments, $R^{17}$ is $C_1$-$C_6$ alkyl.

In some embodiments, $R^{12}$ is $SR^{17}$.

In some embodiments, $R^{12}$ is $NR^{14}R^{15}$. In some embodiments, $R^{12}$ is $NH_2$.

In some embodiments, $R^{13}$ is H. In some embodiments, $R^{13}$ is cyclyl, e.g., a bridged cyclyl such as adamantyl.

Exemplary compounds of Formula (II) include those described in Table 2.

In another aspect, the invention features a method for treating a TRPC5 mediated disorder by administering an effective amount of a compound of Formula (III), or a pharmaceutically acceptable salt thereof:

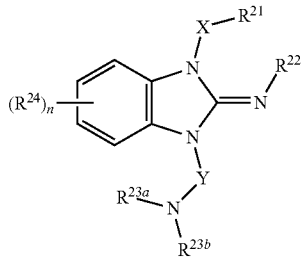

Formula (III)

wherein $R^{21}$ is alkyl, aryl, or heteraryl; each of which is optionally substituted with 1-5 $R^{25}$;

$R^{22}$ is H or $C_1$-$C_6$ alkyl;

each of $R^{23a}$ and $R^{23b}$ is independently $C_1$-$C_6$ alkyl, or $R^{23a}$ and $R^{23b}$ when taken together with the nitrogen to which they are attached form a 4-7 membered ring;

each $R^{24}$ is independently halo, $C_1$-$C_6$ alkyl, nitro, hydroxy, alkoxy, amino, alkylamino, dialkylamino, cyano;

$R^{25}$ is $C_1$-$C_6$ alkyl;

each of X and Y is independently alkylenyl, optionally substituted with 1-3 $R^{26}$;

$R^{26}$ is hydroxyl or alkoxy;

n 0, 1, 2, 3, or 4.

In some embodiments, $R^{21}$ is aryl, for example, phenyl.

In some embodiments, $R^{21}$ is heteroaryl, for example, a 5 membered heteroaryl such as thiophene.

In some embodiments, X is alkylenyl (e.g. ethylenyl), substituted with 1 $R^{26}$. In some embodiments, $R^{26}$ is hydroxyl.

In some embodiments, X is ethylenyl substituted by 1 $R^{26}$. In some embodiments, $R^{26}$ is hydroxyl.

In some embodiments, X is —$CH_2CHOH$—

In some embodiments, $R^{22}$ is H.

In some embodiments, $R^{23a}$ and $R^{23b}$ when taken together with the nitrogen to which they are attached form a ring In some embodiments, Y is ethylene.

In some embodiments, the compound is a compound of formula (IIIa), or a pharmaceutically acceptable salt thereof

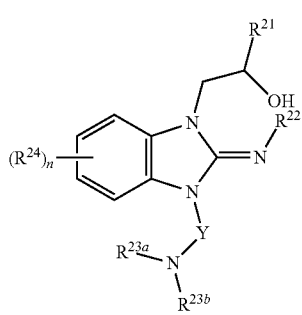

Formula III(a)

Exemplary compounds of Formula (III) include those described in Table 3.

Another aspect of the invention features a pharmaceutical preparation suitable for use in a human patient, or for veterinary use, comprising an effective amount of any of the compounds shown herein, and one or more pharmaceutically acceptable excipients.

DETAILED DESCRIPTION OF THE INVENTION

Cation channels such as TRPC5 modulate the flux of calcium and sodium ions across cellular membranes. Sodium and calcium influx leads to a depolarization of the cell. This increases the probability that voltage-gated ion channels will reach the threshold required for activation. As a result, activation of non-selective cation channels can increase electrical excitability and increase the frequency of voltage-dependent events. Voltage-dependent events include, but are not limited to, neuronal action potentials, cardiac action potentials, smooth muscle contraction, cardiac muscle contraction, and skeletal muscle contraction.

Calcium influx caused by the activation of non-selective cation channels such as TRPC5 also alters the intracellular free calcium concentration. Calcium is a ubiquitous second messenger molecule within the cell and the alterations in intracellular calcium levels have profound effects on signal transduction and gene expression. Thus, activation of non-selective cation channels such as TRPC5 can lead to changes in gene expression and cellular phenotype. Gene expression events include, but are not limited to, production of mRNAs encoding cell surface receptors, ion channels, and kinases. These changes in gene expression can lead to hyperexcitability in that cell.

Transient receptor potential (TRP) homomeric TRPC5 ion channels are receptor-operated, $Ca^{2+}$-permeable channels predominantly expressed in the neurons. TRPC5 forms homomultimeric structures such as tetramers (i.e., TRPC5 homomultimers) and heteromultimeric structures such as tetramers (i.e., TRPC5-TRPC1 heteromultimers). Unless expressly stated otherwise, when the term TRPC5 is used herein, for example, when identifying a modulator of TRPC5 such as a TRPC5 antagonist, the term TRPC5 is used generically so as to include either or both of a TRPC5 homomultimer or a heteromultimer (e.g., TRPC5-TPRC1 or TRPC5-TRPC4 heteromultimer). Examples of TRPC5 in the literature include the following: *Nature*. 2008 Jan. 3; 451(7174):69-72; *Mol Pharmacol*. 2008 January; 73(1):42-9; *J Biol Chem*. 2007 Nov. 16; 282(46):33868-78; *Biochem Biophys Res Commun*. 2008 Jan. 11; 365(2):239-45; *J Biol Chem*. 2006 Nov. 3; 281(44):33487-96; *Eur J Pharmacol*. 2005 Mar. 14; 510(3):217-22; *J Biol Chem*. 2006 Feb. 24; 281(8):4977-82; *Biochem Soc Trans*. 2007 February; 35(Pt 1):101-4; *Handb Exp Pharmacol*. 2007; (179):109-23; *J Biol Chem*. 2005 Mar. 25; 280(12):10997-1006; *J Physiol*. 2006 Jan. 15; 570(Pt 2):219-35; and *Nat Neurosci*. (2003) 6: 837-45.

Modulating the function of TRPC5 proteins provides a means of modulating calcium homeostasis, sodium homeostasis, membrane polarization, and/or intracellular calcium levels, and compounds that can modulate TRPC5 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

In certain aspects, the present invention provides methods for treating or ameliorating the effects of diseases and conditions using a compound describes herein that inhibits a TRPC5-mediated current and/or a TRPC5-mediated ion flux with an $IC_{50}$ of less than 10 micromolar.

In certain embodiments, a TRPC5 antagonist inhibits an inward and/or outward TRPC5 mediated current with an $IC_{50}$ of less than 10 micromolar (e.g., less than 1 micromolar). In certain embodiments, a TRPC5 antagonist inhibits TRPC5 mediated ion flux with an $IC_{50}$ of less than 10 micromolar. The $IC_{50}$ can be calculated, for example, in an in vitro assay. For example, $IC_{50}$ can be calculated using electrophysiological determinations of current, such as standard patch clamp analysis. $IC_{50}$ can also be evaluated using changes in concentration or flux of ion indicators, such as the calcium flux methods described herein.

In some embodiments, a TRPC5 antagonist (e.g., a compound described herein) is chosen because it inhibits a TRPC5 function with an $IC_{50}$ less than or equal to 1 uM, or even less than or equal to 700, 600, 500, 400, 300, 250, 200, or 100 nM. In other embodiments, the small molecule is chosen because it inhibits a TRPC5 function with an $IC_{50}$ less than or equal to 75 nM, less than or equal to 50 nM, or even less than or equal to 25, 10, 5, or 1 nM.

In some embodiments, a TRPC5 antagonist (e.g., a compound described herein) is chosen based on the rate of inhibition of a TRPC5 function. In one embodiment, the compound inhibits a TRPC5 function in less than 5 minutes, preferably less than 4, 3, or 2 minutes. In another embodiment, the compound inhibits a TRPC5 function in less than about 1 minute. In yet another embodiment, the compound inhibits a TRPC5 function in less than about 30 seconds.

In certain embodiments of any of the foregoing, inhibition of a TRPC5 function means that a function, for example a TRPC5 mediated current, is decreased by greater than 50% in the presence of an effective amount of a compound in comparison to in the absence of the compound or in comparison to an ineffective amount of a compound. In certain other embodiments, the inhibition of a TRPC5 function means that a function, for example a TRPC5 mediated current or TRPC5 mediated ion flux, is decreased by at least 50%, 60%, 70%, 75%, 80%, 85%, or 90% in the presence of an effective amount of a compound in comparison to in the absence of the compound. In still other embodiments, the inhibition of a TRPC5 function means that a function, for example a TRPC5 mediated current, is decreased by at least 92%, 95%, 97%, 98%, 99%, or 100% in the presence of an effective amount of a compound in comparison to in the absence of the compound.

In certain embodiments, a TRPC5 antagonist (e.g., a compound described herein) is chosen for use because it is more potent against TRPC5 than for other TRP ion channels, (including, but not limited to, TRPV5, TRPV3, TRPV4, TRPM8, TRPA1, TRPC3, TRPV6, TRPC7, TRPV6, and TRPV1). For example, the TRPC5 antagonist can be 10-fold, and more preferably at least 20, 40, 50, 60, 70, 80, or at least 100-fold or at least 1000-fold more potent against TRPC5 than for the other TRP channel.

The TRPC5 antagonist can also be more potent against TRPC5 than against NaV1.2, Cav1.2, Cav3.1, hERG, and/or the mitochondrial uniporter.

In certain embodiments, a TRPC5 antagonist (e.g., a compound described herein) has a therapeutic index (T.I.) for treating the condition with the compound of 3 or greater, and more preferably has a T.I. of at least 5, 10, 25, 50 or 100.

Exemplary compounds are provided in Tables 1-3, below:

TABLE 1

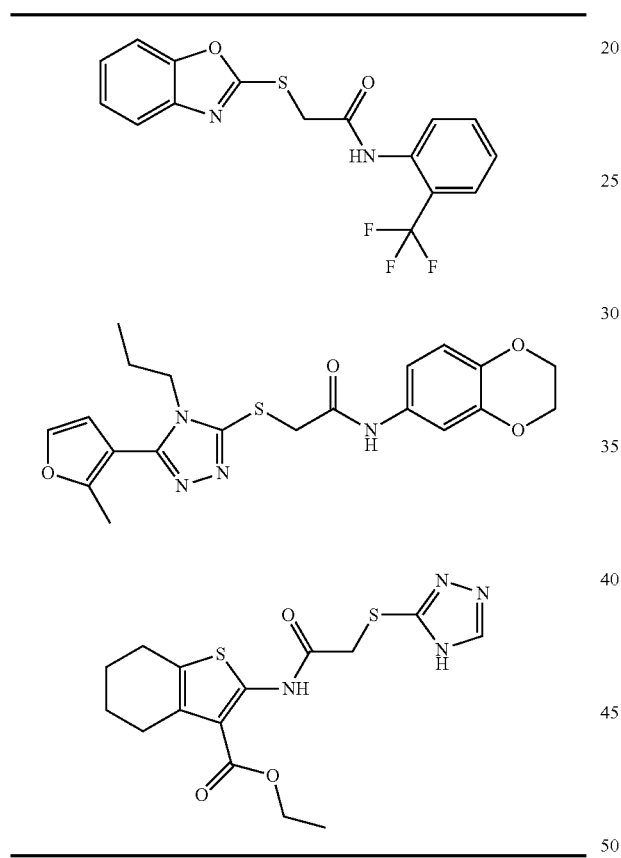

TABLE 2

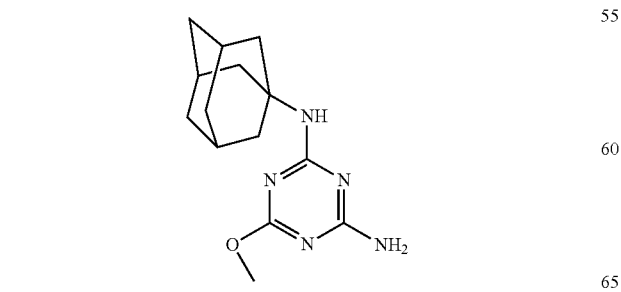

TABLE 2-continued

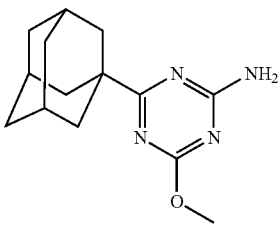 [SMILES: COc1nc(N)nc(C23CC4CC(CC(C4)C2)C3)n1]

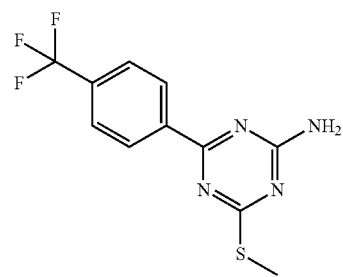 [SMILES: CSc1nc(N)nc(-c2ccc(C(F)(F)F)cc2)n1]

TABLE 3

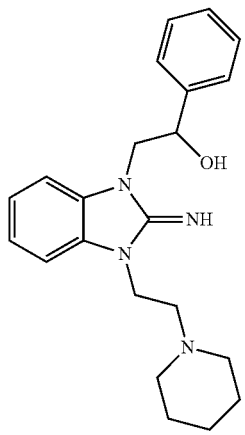 [SMILES: N=c1n(CCN2CCCCC2)c2ccccc2n1CC(O)c1ccccc1]

TABLE 3-continued

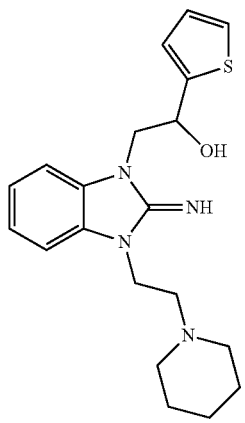 [SMILES: N=c1n(CCN2CCCCC2)c2ccccc2n1CC(O)c1cccs1]

Compounds of any of the above structures may be used to inhibit a function of a TRPC5 channel in vitro or in vivo.

Definitions

The term "acyl" is art-recognized and refers to a group represented by the general formula hydrocarbylC(O)—, preferably alkylC(O)—.

The term "acylamino" is art-recognized and refers to a moiety that can be represented by the general formula:

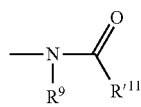

wherein $R^9$ is as defined above, and $R'^{11}$ represents a hydrogen, an alkyl, an alkenyl or —(CH$_2$)m-R$^8$, where m and R$^8$ are as defined above.

The term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkenyl", as used herein, refers to an aliphatic group containing at least one double bond.

The terms "alkoxyl" or "alkoxy" as used herein refers to an alkyl group, as defined below, having an oxygen radical attached thereto. Representative alkoxyl groups include methoxy, ethoxy, propyloxy, tert-butoxy and the like. An "ether" is two hydrocarbons covalently linked by an oxygen.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer, and most preferably 10 or fewer. Likewise, preferred cycloalkyls have from 3-10 carbon atoms in their ring structure, and more preferably have 5, 6 or 7 carbons in the ring structure.

The term "alkynyl", as used herein, refers to an aliphatic group containing at least one triple bond.

The term "alkylthio" refers to an hydrocarbyl having a sulfur radical attached thereto. In preferred embodiments, the "alkylthio" moiety is represented by one of —S-alkyl, —S-alkenyl, —S-alkynyl. Representative alkylthio groups include methylthio, ethylthio, and the like.

The terms "amine" and "amino" are art-recognized and refer to both unsubstituted and substituted amines, e.g., a moiety that can be represented by the general formula:

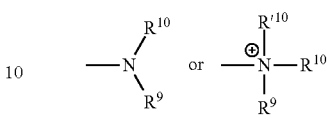

wherein $R^9$, $R^{10}$ and $R'^{10}$ each independently represent a hydrogen, an alkyl, an alkenyl, —(CH$_2$)$_m$—R$^8$, or $R^9$ and $R^{10}$ taken together with the N atom to which they are attached complete a heterocycle having from 4 to 8 atoms in the ring structure; $R^8$ represents an aryl, a cycloalkyl, a cycloalkenyl, a heterocycle or a polycycle; and m is zero or an integer in the range of 1 to 8.

The term "amido" refers to a moiety that can be represented by the general formula:

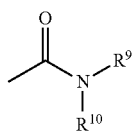

wherein $R^9$, $R^{10}$ are as defined above.

The term "aralkyl", as used herein, refers to an alkyl group substituted with an aryl group (e.g., an aromatic or heteroaromatic group).

The term "aryl" as used herein includes 5-, 6-, and 7-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, polycyclyl, hydroxyl, alkoxyl, amino, nitro, sulfhydryl, imino, amido, phosphate, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "carbocycle or cycyl", as used herein, refers to an aromatic or non-aromatic ring in which each atom of the ring is carbon.

The term "carbonyl" refers to moieties represented by the general formula:

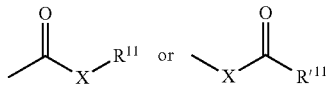

wherein X is a bond or represents an oxygen or a sulfur, and $R^{11}$ represents a hydrogen, an alkyl, an alkenyl, —$(CH_2)_m$—$R^8$ or a pharmaceutically acceptable salt, $R'^{11}$ represents a hydrogen, an alkyl, an alkenyl or —$(CH_2)_m$—$R^8$, where m and $R^8$ are as defined above. Where X is an oxygen and $R^{11}$ or $R'^{11}$ is not hydrogen, the formula represents an "ester". Where X is an oxygen, and $R^{11}$ is as defined above, the moiety is referred to herein as a carboxyl group, and particularly when $R^{11}$ is a hydrogen, the formula represents a "carboxylic acid". Where X is an oxygen, and $R'^{11}$ is hydrogen, the formula represents a "formate". In general, where the oxygen atom of the above formula is replaced by sulfur, the formula represents a "thiocarbonyl" group. Where X is a sulfur and $R^{11}$ or $R'^{11}$ is not hydrogen, the formula represents a "thioester." Where X is a sulfur and $R^{11}$ is hydrogen, the formula represents a "thiocarboxylic acid." Where X is a sulfur and $R^{11\prime}$ is hydrogen, the formula represents a "thiolformate." On the other hand, where X is a bond, and $R^{11}$ is not hydrogen, the above formula represents a "ketone" group. Where X is a bond, and $R^{11}$ is hydrogen, the above formula represents an "aldehyde" group.

The term "ester", as used herein, refers to a group —C(O)$OR^9$ wherein $R^9$ represents a hydrocarbyl group.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heterocyclyl" or "heterocyclic group" refer to 3- to 10-membered ring structures, more preferably 3- to 7-membered rings, whose ring structures include one to four heteroatoms. Heterocycles can also be polycycles, with each group having, e.g., 5-7 ring members. The term "heterocyclyl" or "heterocyclic group" includes "heteroaryl" and "saturated or partially saturated heterocyclyl" structures. The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively). Any ring atom can be substituted (e.g., by one or more substituents). The term "saturated or partially saturated heterocyclyl" refers to a non-aromatic cylic structure that includes at least one heteroatom. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

As used herein, the term "nitro" means —$NO_2$; the term "halogen" or "halo" designates —F, —Cl, —Br or —I; the term "sulfhydryl" means —SH; the term "hydroxyl" means —OH; and the term "sulfonyl" means —$SO_2$—.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

Exemplary monocyclic rings include furan, thiophene, pyrrole, pyrroline, pyrrolodine, oxazole, thiazole, imidazole, imidazoline, pyrazole, pyrazoline, pyrazolidine, isoxazole, isothiazole, oxadiazole, triazole, thiadiazole, pyran, pyridine, piperidine, dioxane, morpholine, dithiane, thiomorpholine, pyridazine, pyrimidine, pyrazine, piperazine, triazine, and trithiane.

Exemplary bicyclic rings include indolizinyl, indolyl, isoindolyl, indolinyl, benzofuranyl, benzothiophenyl, indazolyl, benzimidazolyl, benthiazolyl, purinyl, quinolizinyl, quinolinyl, isoquinolinyl, cinnolinyl, phthalazinyl, quinazolinyl, quinoxalinyl, naphthyridinyl, pteridinyl, indenyl, naphthalenyl, azulenyl, imidazopyridazionyl, pyrazolopyrimidinedionyl, or pyrrolopyrimidinedionyl moieties.

Exemplary tricyclic rings include carbazole, acridine, phenazine, phenothiazine, phenoxazine, fluorine, and anthracene.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis*, $2^{nd}$ ed.; Wiley: New York, 1991).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like. Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

The term "sulfate" refers to a moiety that can be represented by the general formula:

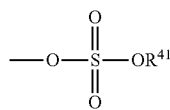

in which $R^{41}$ is as defined above.

The term "sulfonamido" refers to a moiety that can be represented by the general formula:

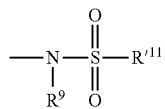

in which $R^9$ and $R'^{11}$ are as defined above.

The term "sulfonate" refers to a moiety that can be represented by the general formula:

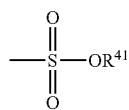

in which $R^{41}$ is an electron pair, hydrogen, alkyl, cycloalkyl, or aryl.

The terms "sulfoxido" or "sulfinyl", as used herein, refers to a moiety that can be represented by the general formula —S(=O)—$R^{44}$, in which $R^{44}$ is selected from the group consisting of hydrogen, alkyl, alkenyl, alkynyl, cycloalkyl, heterocyclyl, aralkyl, or aryl.

The term "thioester", as used herein, refers to a group —C(O)S$R^9$ or —SC(O)$R^9$ wherein $R^9$ represents a hydrocarbyl.

As used herein, the definition of each expression, e.g., alkyl, m, n, etc., when it occurs more than once in any structure, is intended to be independent of its definition elsewhere in the same structure.

Certain compounds disclosed herein may exist in particular geometric or stereoisomeric forms. The present invention contemplates all such compounds, including cis- and trans-isomers, R- and S-enantiomers, diastereomers, (d)-isomers, (l)-isomers, the racemic mixtures thereof, and other mixtures thereof, as falling within the scope of the invention. For example, if one chiral center is present in a molecule, the invention includes racemic mixtures, enantiomerically enriched mixtures, and substantially enantiomerically pure compounds. The composition can contain, e.g., more than 50%, more than 60%, more than 70%, more than 80%, more than 90%, more than 95%, or more than 99% of a single enantiomer.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%. Compositions have ee's of at least 90%, 95%, 98%, 99%, 99.5%, and 99.9% are included within the scope of the invention.

Methods of preparing substantially isomerically pure compounds are known in the art. If, for instance, a particular enantiomer of a compound disclosed herein is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts may be formed with an appropriate optically active acid or base, followed by resolution of the diastereomers thus formed by fractional crystallization or chromatographic means well known in the art, and subsequent recovery of the pure enantiomers. Alternatively, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Techniques for inverting or leaving unchanged a particular stereocenter, and those for resolving mixtures of stereoisomers are well known in the art, and it is well within the ability of one of skill in the art to choose an appropriate method for a particular situation. See, generally, Furniss et al. (eds.), *Vogel's Encyclopedia of Practical Organic Chemistry* 5$^{th}$ *Ed.*, Longman Scientific and Technical Ltd., Essex, 1991, pp. 809-816; and Heller, *Acc. Chem. Res.* 23: 128 (1990).

Contemplated equivalents of the compounds described above include compounds which otherwise correspond thereto, and which have the same general properties thereof (e.g., the ability to inhibit TRPC5 activity), wherein one or more simple variations of substituents are made which do not adversely affect the efficacy of the compound. In general, the compounds disclosed herein may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

The compounds described herein may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds disclosed herein, whether radioactive or not, are intended to be encompassed within the scope of the present invention. For example, deuterated compounds and compounds incorporating $^{13}$C are intended to be encompassed within the scope of the invention.

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

As set out above, certain embodiments of the present compounds may contain a basic functional group, such as amino or alkylamino, and are thus capable of forming pharmaceutically acceptable salts with pharmaceutically acceptable acids. The term "pharmaceutically acceptable salts" in this respect, refers to the relatively non-toxic, inorganic and organic acid addition salts of compounds disclosed herein. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19.)

In other cases, the compounds disclosed herein may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds disclosed herein. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

The terms "antagonist" and "inhibitor" are used interchangeably to refer to an agent that decreases or suppresses a biological activity, such as to repress an activity of an ion channel, such as TRPC5. TRPC5 inhibitors include inhibitors having any combination of the structural and/or functional properties disclosed herein.

An "effective amount" of, e.g., a TRPC5 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPC5 antagonist for use in the methods of the present invention, includes an amount of a TRPC5 antagonist effective to decrease one or more in vitro or in vivo functions of a TRPC5 channel. Exemplary functions include, but are not limited to, membrane polarization (e.g., an antagonist may promote hyperpolarization of a cell), ion flux, ion concentration in a cell, outward current, and inward current. Compounds that antagonize TRPC5 function include compounds that antagonize an in vitro or in vivo functional activity of TRPC5. When a particular functional activity is only readily observable in an in vitro assay, the ability of a compound to inhibit TRPC5 function in that in vitro assay serves as a reasonable proxy for the activity of that compound. In certain embodiments, an effective amount is an amount sufficient to inhibit a TRPC5-mediated current and/or the amount sufficient to inhibit TRPC5 mediated ion flux.

The term "hydrate" as used herein, refers to a compound formed by the union of water with the parent compound.

The term "oxidative metabolite" is intended to encompass compounds that are produced by metabolism of the parent compound under normal physiological conditions. Specifically, an oxidative metabolite is formed by oxidation of the parent compound during metabolism. For example, a thioether group may be oxidized to the corresponding sulfoxide or sulfone.

The term "preventing," when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity in the host animal.

The term "solvate" as used herein, refers to a compound formed by solvation (e.g., a compound formed by the combination of solvent molecules with molecules or ions of the solute).

The terms "TRPC5", "TRPC5 protein", and "TRPC5 channel" are used interchangeably throughout the application. Unless expressly stated, the term TRPC5 includes homomultimeric structures (e.g., homomultimeric TRPC5) and heteromultimeric structures (e.g., heteromultimeric TRPC5-TRPC1).

Diseases, Disorders, or Conditions Related to TRPC5 Function

In certain embodiments, the invention provides methods and compositions for antagonizing a function of a TRPC5 channel in vitro or in vivo. Exemplary functions include, but are not limited to, TRPC5-mediated current. In certain embodiments, the invention provides methods for treating a disease or disorder or condition by administering an agent that modulates the level and/or activity of a TRPC5 protein. In other embodiments, the compound selectively inhibits the expression level and/or activity of a TRPC5 protein. In other words, in certain embodiment, the compound inhibits the activity of a TRPC5 protein preferentially in comparison to the activity of one or more other ion channels.

Treatment of Anxiety and Fear-Related Disorders

In certain embodiments, the TRPC5 antagonist can be used for preventing or treating anxiety and fear-related disorders (see, e.g., Riccio et al. (2009) Cell 137:761-72). Examples of such disorders include post-traumatic stress disorder, panic disorder, agoraphobia, social phobias, generalized anxiety disorder, panic disorder, social anxiety disorder, obsessive-compulsive disorder, and separation anxiety.

Memory, Motion, and Mood Disorders

A TRPC5 antagonist (e.g., a compound described herein) is also useful for the treatment of Parkinson's disease, epilepsy, memory disorders, stroke, seizure, and mood disorders. Mood disorders include depression (e.g., major depression, psychiatric depression, dysthymia, and postpartum depression) and bipolar disorder (e.g., bipolar I, bipolar II, and cyclothymia). Memory disorders are conditions associated with any memory loss and may result from Alzheimer's disease, amnesia, aphasia, atherosclerosis, brain injury or disorder, brain tumor, chronic fatigue syndrome, Creutzfedt-Jacob disease, dissociative amnesia, depression, fuge amnesia, Huntington's disease, learning disorders, sleeping disorders, multiple personality disorder, pain, post-traumatic stress disorder, schizophrenia, sports injuries, stroke, and Wernicke-Korsakoff syndrome.

Treatment of Pain, Sensitivity to Pain and Touch, or Pain-Related Diseases or Disorders In certain embodiments, the TRPC5 inhibitor is used to treat or ameliorate pain. Exemplary classes of pain that can be treated using a TRPC5 inhibitor include, but are not limited to nociceptive pain, inflammatory pain, and neuropathic pain. The pain can be chronic or acute.

TRPC5 inhibitors may be particularly useful in the treatment of pain associated with cancer, osteoarthritis, rheumatoid arthritis, post-herpetic neuralgia, burns, and other indications detailed above. To further illustrate, additional exemplary indications for which compounds disclosed herein can be used include oral pain, pelvic pain, Fabry's disease, complex regional pain syndrome, pancreatitis, and fibromyalgia syndrome.

The compounds disclosed herein may also be used in connection with prevention or treatment of sensitivity to pain and touch. Pain or sensitivity to pain and touch may be indicated in a variety of diseases, disorders or conditions, including, but not limited to, diabetic neuropathy, breast pain, psoriasis, eczema, dermatitis, burn, post-herpetic neuralgia (shingles), nociceptive pain, peripheral neuropathic and central neuropathic pain, chronic pain, cancer and tumor pain, spinal cord injury, crush injury and trauma induced pain, migraine, cerebrovascular and vascular pain, sickle cell disease pain, rheumatoid arthritis pain, musculoskeletal pain including treating signs and symptoms of osteoarthritis and rheumatoid arthritis, orofacial and facial pain, including dental, temperomandibular disorder, and cancer related, lower back or pelvic pain, surgical incision related pain, inflammatory and non-inflammatory pain, visceral pain, psychogenic pain and soft tissue inflammatory pain, fibromyalgia-related pain, and reflex sympathetic dystrophy, and pain resulting from kidney stones or urinary tract infection.

Oral pain is a particular category of pain that may be treated using the TRPC5 inhibitors disclosed herein. The term "oral pain" refers to any pain in the mouth, throat, lips, gums, teeth, tongue, or jaw. The term is used regardless of the cause of the pain and regardless of whether the oral pain is a primary or secondary symptom of a particular disease, injury, or condition.

In certain embodiments, oral pain is caused by ulcers, sores, or other lesions in the mouth. For example, oral pain may be caused by ulcers, sores, or other lesions on the tongue, gums, lips, throat, or other tissues of the mouth. Alternatively or additionally, oral pain may be caused by inflammation of the throat, tongue, gums, lips, or other tissues of the mouth. Inflammation may accompany ulcers or other lesions, or inflammation may occur prior to or in the absence of formation of ulcers or other lesions.

The foregoing are merely exemplary of diseases and conditions that cause or lead to inflammation, lesions, ulcers, or other sources of oral pain. In other embodiments, the oral pain is due to an injury to the mouth, jaw, lips, gums, or teeth. In other embodiments, the oral pain is due to oral surgery, for example, surgery for cancer, tooth extraction, or jaw remodeling. Other conditions that may lead to oral ulcers, and thus oral pain, include, but are not limited to chickpox, herpes zoster, infectious mononucleosis, syphilis, tuberculosis, acute necrotizing gingivitis, and burning mouth syndrome.

Fibromyalgia (FMS; fibromyalgia syndrome) is a widespread musculoskeletal pain and fatigue disorder. Fibromyalgia is characterized by pain in the muscles, ligaments, and tendons. The condition affects more women than men, and occurs in people of all ages. Overall, FMS is estimated to afflict 3-6% of the population. Patients have described the pain associated with fibromyalgia as deep muscular aching, throbbing, shooting, and stabbing. The pain sometimes includes an intense burning sensation. The pain and stiffness are often worse in the morning or after repetitive use of a particular muscle group.

Additionally, varying levels of fatigue ranging from mild to incapacitating are often associated with fibromyalgia. Other symptoms of fibromyalgia include gastrointestinal symptoms. Irritable bowel syndrome and IBS-like symptoms such as constipation, diarrhea, frequent abdominal pain, abdominal gas, and nausea occur in roughly 40 to 70% of FMS patients. Acid reflux or gastroesophogeal reflux disease (GERD) occurs at a similar frequency.

Complex Regional Pain Syndrome (CRPS; also known as chronic regional pain syndrome) is a chronic pain condition. CRPS was formerly known as reflex sympathetic dystrophy (RSD). CRPS is a chronic, painful, and progressive neurological condition that affects skin, muscles, joints, and bones. The syndrome usually develops in an injured limb, such as a broken leg or following surgery. However, many cases involve only a minor injury, such as a sprain, and sometimes no precipitating injurious event can be identified. CRPS involves continuous, intense pain that is disproportionate to the severity of the injury. The pain worsens, rather than improves, over time.

Although CRPS can affect a variety of regions of the body, it most often affects the arms, legs, hands, or feet. Often the pain begins in one portion of a limb, but spreads over time to include the entire limb or even to include a different limb. Typical features include dramatic changes in the color and temperature of the skin over the affected limb or body part, accompanied by intense burning pain, skin sensitivity, sweating, and swelling.

The compounds disclosed herein can also be used to treat endometriosis and the pain associated therewith.

Respiratory Disorders

The compounds described herein are useful for the treatment or prevention of respiratory conditions. Such conditions affect the lung, pleural cavity, bronchial tubes, trachea, upper respiratory tract as well as the nerves and muscles involved in breathing. Respiratory diseases that may be treated with the compounds described herein include obstructive diseases such as chronic obstructive pulmonary disease (COPD), chronic cough, emphysema, chronic bronchitis, asthma (including asthma caused by industrial irritants), cystic fibrosis, bronchiectasis, bronchiolitis, allergic bronchopulmonary aspergillosis, and tuberculosis; restrictive lung disease including asbestosis, radiation fibrosis, hypersensitivity pneumonitis, infant respiratory distress syndrome, idiopathic pulmonary fibrosis, idiopathic pulmonary fibrosis, idiopathic interstial pneumonia sarcoidosis, eosinophilic pneumonia, lymphangioleiomyomatosis, pulmonary Langerhan's cell histiocytosis, and pulmonary alveolar proteinosis; respiratory tract infections including upper respiratory tract infections (e.g., common cold, sinusitis, tonsillitis, pharyngitis and laryngitis) and lower respiratory tract infections (e.g., pneumonia); respiratory tumors whether malignant (e.g., small cell lung cancer, non-small cell lung cancer, adenocarcinoma, squamous cell carcinoma, large cell undifferentiated carcinoma, carcinoid, mesothelioma, metastatic cancer of the lung, metastatic germ cell cancer, metastatic renal cell carcinoma) or benign (e.g., pulmonary hamartoma, congenital malformations such as pulmonary sequestration and congenital cystic adenomatoid malformation (CCAM)); pleural cavity diseases (e.g., empyema and mesothelioma); and pulmonary vascular diseases (e.g, pulmonary embolism such as thromboembolism, and air embolism (iatrogenic), pulmonary arterial hypertension, pulmonary edema, pulmonary hemorrhage, inflammation and damage to capillaries in the lung resulting in blood leaking into the alveoli. Other conditions that may be treated include disorders that affect breathing mechanics (e.g., obstructive sleep apnea, central sleep apnea, amyotrophic lateral sclerosis, Guillan-Barre syndrome, and myasthenia gravis). The present compounds can also be useful for treating, reducing, or preventing one or more symptoms associated with respiratory conditions including, for example, shortness of breath or dyspnea, cough (with or without the production of sputum), cough associated with asthma, cough associated with influenza, coughing blood (haemoptysis), chest pain including pleuritic chest pain, noisy breathing, wheezing, and cyanosis.

Neurological or Neurodegenerative Diseases and Disorders

Neurodegenerative diseases and disorders include but are not limited to Alzheimer's disease (AD), Parkinson's disease, Huntington's disease, amyotrophic lateral sclerosis (ALS), and other brain disorders caused by trauma or other insults including aging.

Mechanisms associated with calcium signaling may be altered in many neurodegenerative diseases and in disorders resulting from brain injury. For example, fibroblasts or T-lymphocytes from patients with AD have consistently displayed an increase in $Ca^{2+}$ release from intracellular stores compared to controls (Ito et al. (1994) Proc. Natl. Acad. Sci. U.S.A. 91:534-538; Gibson et al. (1996) Biochem. Biophys. ACTA 1316:71-77; Etchenberrigaray et al. (1998) Neurobiology of Disease, 5:37-45). Consistent with these observations, mutations in presenilin genes (PS1 or PS2) associated with familial AD (FAD) have been shown to increase InsP3-mediated $Ca^{2+}$ release from internal stores (Guo et al. (1996) Neuro Report, 8:379-383; Leissring et al. (1999) J. Neurochemistry, 72:1061-1068; Leissring et al. (1999) J. Biol. Chem. 274(46):32535-32538; Leissring et al. (2000) J. Cell Biol. 149(4):793-797; Leissring et al. (2000) Proc. Natl. Acad. Sci. U.S.A. 97(15):8590-8593). Furthermore, mutations in PS1 or PS2 associated with an increase in amyloidogenic amyloid β peptide generation in AD are reported to be associated with a decrease in intracellular calcium level (Yoo et al. (2000) Neuron, 27(3):561-572).

Experimental traumatic brain injury has been shown to initiate massive disturbances in $Ca^{2+}$ concentrations in the brain that may contribute to further neuronal damage. Intracellular $Ca^{2+}$ may be elevated by many different ion channels. It has been further shown that channel blockers may be beneficial in the treatment of neurological motor dysfunction when administered in the acute posttraumatic period (Cheney et al. (2000) J. Neurotrauma, 17(1):83-91).

Incontinence

Incontinence is a significant social and medical problem affecting both men and women. Incontinence has many causes including, but not limited to, age, pregnancy, radiation exposure, surgery, injury, cancer, enlargement of the prostatic, prostatic hyperplasia, and diseases of the bladder or musculature that supports the urethra. The invention contemplates methods for treating incontinence due to any of the foregoing, as well as incontinence of unknown cause or continence due to anxiety, stress, or depression.

In certain embodiments, the compounds disclosed herein are used to reduce bladder hyperactivity by decreasing the activity of the neurons that innervate the bladder. In certain embodiments, incontinence is accompanied by pain. For example, incontinence incident to bladder cystitis or incontinence incident to an injury may be accompanied by pain. When incontinence is accompanied by pain, the compound may be administered to treat both incontinence and to reduce pain.

the sensation of cool, cold and decreased temperatures that often accompany pain.

Combination Therapy

The present invention provides TRPC5 inhibitors for use in vitro and in vivo. The present invention also provides compositions and pharmaceutical compositions comprising particular classes of compounds that inhibit TRPC5 activity. In certain embodiments, the subject TRPC5 inhibitors are selective. In other words, in certain embodiments, the compound inhibits TRPC5 activity preferentially over the activity of other ion channels. In certain embodiments, the compound inhibits TRPC5 activity preferentially over TRPV1, TRPV2, TRPV3, TRPV4, TRPC3, TRPC6, TRPC7, TRPA1, and/or TRPM8 activity. In certain other embodiments, the compound is selected because it cross reacts with one or more other TRP channels involved with pain. For example, in certain embodiments, the compound inhibits the activity of TRPC5 and also inhibits the activity of one or more of TRPV1, TRPV2, TRPV3, TRPV4, TRPC3, TRPC6, TRPC7, TRPA1, and TRPM8.

TRPC5 antagonists can be used alone or in combination with other pharmaceutically active agents. Examples of such other pharmaceutically active agents include, but are not limited to, anti-depressants, anti-anxiety agents, anti-epileptic agents, anti-inflammatory agents (e.g., NSAIDS, bradykinin receptor antagonists, hormones and autacoids such as corticosteroids), anti-acne agents (e.g., retinoids), anti-wrinkle agents, anti-scarring agents, anti-incontinence agents (such as M1-receptor antagonists) anti-emetics (such as NK1 antagonists), anti-psoriatic agents, antacids, anti-proliferative agents (e.g., anti-eczema agents, anti-cancer), anti-fungal agents, anti-viral agents, anti-septic agents (e.g., antibacterials), local anaesthetics, anti-migraine agents, keratolytic agents, hair growth stimulants, hair growth inhibitors, and other agents used for the treatment of skin diseases or conditions. Certain active agents belong to more than one category.

In certain embodiments, a compound of the invention is conjointly administered with an analgesic. Suitable analgesics include, but are not limited to, opioids, glucocorticosteroids, non-steroidal anti-inflammatories, naphthylalkanones, oxicams, para-aminophenol derivatives, propionic acids, propionic acid derivatives, salicylates, fenamates, fenamate derivatives, pyrozoles, and pyrozole derivatives. Examples of such analgesic compounds include, but are not limited to, codeine, hydrocodone, hydromorphone, levorpharnol, morphine, oxycodone, oxymorphone, butorphanol, dezocine, nalbuphine, pentazocine, etodolac, indomethacin, sulindac, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid, mefanamic acid, prednisolone, and dexamethasone. Preferred analgesics are non-steroidal anti-inflammatories and opioids (preferably morphine).

In some embodiments, the compounds disclosed herein can be administered in conjunction with a therapeutic whose administration causes pain. For example, a compound described herein can be administered in conjunction with an anesthetic, to reduce the pain caused by the administration of the anaesthetic. A compound described herein can also be administered in conjunction with a chemotherapeutic agent, to reduce the pain caused by administration of the chemotherapeutic agent.

In certain embodiments, a compound of the invention is conjointly administered with a non-steroidal anti-inflammatory. Suitable non-steroidal anti-inflammatory compounds include, but are not limited to, piroxicam, diclofenac, etodolac, indomethacin, ketoralac, oxaprozin, tolmetin, naproxen, flubiprofen, fenoprofen, ketoprofen, ibuprofen, mefenamic acid, sulindac, apazone, phenylbutazone, aspirin, celecoxib and rofecoxib.

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

The tablets, and other solid dosage forms of the pharmaceutical compositions disclosed herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The formulations disclosed herein can be delivered via a device. Exemplary devices include, but are not limited to, a catheter, wire, stent, or other intraluminal device. Further exemplary delivery devices also include a patch, bandage, mouthguard, or dental apparatus. Transdermal patches have the added advantage of providing controlled delivery of a compound disclosed herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, drops, solutions and the like, are also contemplated as being within the scope of this invention.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

One specific embodiment is an antitussive composition for peroral administration comprising an agent that inhibits both a TRPC5-mediated current with an $IC_{50}$ of 1 micromolar or less, and an orally-acceptable pharmaceutical carrier in the form of an aqueous-based liquid, or solid dissolvable in the mouth, selected from the group consisting of syrup, elixer, suspension, spray, lozenge, chewable lozenge, powder, and chewable tablet. Such antitussive compositions can include one or more additional agents for treating cough, allergy or asthma symptom selected from the group consisting of: antihistamines, 5-lipoxygenase inhibitors, leukotriene inhibitors, H3 inhibitors, β-adrenergic receptor agonists, xanthine derivatives, α-adrenergic receptor agonists, mast cell stabilizers, expectorants, NK1, NK2 and NK3 tachykinin receptor antagonists, and $GABA_B$ agonists.

Still another embodiment is a metered dose aerosol dispenser containing an aerosol pharmaceutical composition for pulmonary or nasal delivery comprising an agent that inhibits a TRPC5-mediated current with an $IC_{50}$ of 1 micromolar or less. For instance, it can be a metered dose inhaler, a dry powder inhaler or an air-jet nebulizer.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. For example, the dose can be 0.1-50, 0.1-25, 0.5-10, 1-10, or 5-10 mg/kg.

If desired, the effective daily dose of the active compound may be administered as two, three, four, five, six or more sub-doses administered separately at appropriate intervals throughout the day, optionally, in unit dosage forms.

Disease and Injury Models

Compounds that antagonize TRPC5 function may be useful in the prophylaxis and treatment of any of the foregoing injuries, diseases, disorders, or conditions. In addition to in vitro assays of the activity of these compounds, their efficacy can be readily tested in one or more animal models. By way of example, numerous well known animal models exist. One or more suitable animal models (e.g., suitable in light of the particular indication) can be selected.

Fear-related behaviors can be measured as described, e.g., in Riccio et al. Pain behaviors can be studied using various agents or procedures to simulate pain resulting from injuries, diseases, or other conditions. Blackburn-Munro (2004) Trends in Pharmacological Sciences 25: 299-305 (see, for example, Table 1). Behavioral characteristics of challenged animals can then be observed. Compounds or procedures that may reduce pain in the animals can be readily tested by observing behavioral characteristics of challenged animals in the presence versus the absence of the test compound(s) or procedure.

Exemplary behavioral tests used to study chronic pain include tests of spontaneous pain, allodynia, and hyperalgesia. Id. To assess spontaneous pain, posture, gait, nocifensive signs (e.g., paw licking, excessive grooming, excessive exploratory behavior, guarding of the injured body part, and self-mutilation) can be observed. To measure evoked pain, behavioral responses can be examined following exposure to heat (e.g., thermal injury model).

Exemplary animal models of pain include, but are not limited to, the Chung model, the carageenan induced hyperalgesia model, the Freund's complete adjuvant induced hyperalgesia model, the thermal injury model, the formalin model and the Bennett Model. The Chung model of neuropathic pain (without inflammation) involves ligating one or more spinal nerves. Chung et al. (2004) Methods Mol Med 99: 35-45; Kim and Chung (1992) Pain 50: 355-363. Ligation of the spinal nerves results in a variety of behavioral changes in the animals including heat hyperalgesia, cold allodynia, and ongoing pain. Compounds that antagonize TRPC5 can be administered to ligated animals to assess whether they diminish these ligation-induced behavioral changes in comparison to that observed in the absence of compound.

Useful anxiety and depression models include the maternal separation model, the elevated plus-maze model, the forced swim test, the tail suspension test, the light/dark preference model, the light-enhanced startle model, and the ultrasonic vocalization model.

Example 1: High Throughput Screening Assay

The assay depended on detection of the rise in intracellular $Ca^{2+}$ concentration ($[Ca^{2+}]_i$) following channel activation in cells inducibly expressing the TRPC5 channel. $Ca^{2+}$ rise was quantified with the use of fluorescent $Ca^{2+}$ indicators that were loaded into cells and thereafter indicated the $[Ca^{2+}]_i$. $Ca^{2+}$ influx followed activation of the TRPC5 channel. Compounds inhibiting the $[Ca^{2+}]_i$ rise were considered hits for further investigation.

The commercially available HEK293/TREx line (Invitrogen) was stably transfected with a TRPC5 construct and screened by conventional calcium imaging to find clones with TRPC5 expression following stimulation with 1 μg/ml tetracycline. These cells were maintained in the growth medium recommended by the manufacturer supplemented with 100 μg/ml hygromycin to promote retention of the TRPC5 construct. After growing to near confluency, cells were plated at a density of ~35,000 cells/well in 384 well CellBind plates (Corning) in the presence of 1 μg/ml tetracycline, and allowed to grow for 20-30 hrs. A nearly confluent monolayer resulted. Cells were then loaded with $Ca^{2+}$ dye: Fura-2/AM or Fluo4/AM was added to the wells to a final concentration of 4 μM or 0.5 μM, respectively, and incubated for 80 min or 60 min, respectively, at room temperature. Supernatant was then removed from the cells by inverting plates with a sharp flick, and 40 μl Hank's Balanced Salt Solution (HBSS; 0.185 g/l D-glucose, 0.9767 g/l $MgSO_4$ (anhydrous), 0.4 g/l KCl, 0.06 g/l $KH_2PO_4$ (anhydrous), 0.35 g/l $NaHCO_3$, 8.0 g/l NaCl, and 0.04788 g/l $Na_2HPO_4$ (anhydrous); pH 7.4) was then added to each well. Following ~0.5 hour for recovery from loading, cells were assayed using the Hamamatsu FDSS 6000 system, which permitted illumination alternately at 340 nm and 380 nm for Fura-2 experiments, or at 485 nm for Fluo4 experiments. Frames were acquired at a rate of 0.2 Hz. During the assay, the plates were continuously vortexed, with pipette mixing of wells following addition of each reagent. For the screening assay, 13 μl of a diluted compound stock (at 50 μM) was added to each well for 2 minutes following the collection of a short (4 frame) baseline. 13 μl 62 mM high-$Ca^{2+}$ Ringer solution (4.17 ml of normal ringer (with 2 mM Ca²⁺) plus 5.83 ml of isotonic calcium ringer (105 mM Ca²⁺; in this ringer all sodium has been replaced with calcium)) was then added to each well, achieving a final concentration of 14 mM Ca²⁺ and 10 µM test compound. Data was collected for ~3 minutes following addition of high Ca²⁺ Ringer, where the fluorescent intensity (for Fluo4) and the F340/F380 ratio (for Fura-2) were proportional to the [Ca²⁺]$_i$. Negative controls consisted of HEK293/TREx TRPC5 cells exposed to high Ca²⁺ solution, but no compound. Positive control conditions consisted of addition of 2-APB, a promiscuous blocker of TRPC5 and other channels, to columns 23 and 24 of the plates, to a final concentration of 200 µM. These controls defined a screening window, and "hits" were defined as those compounds inhibiting the fluorescence response by at least 40%. IC$_{50}$ values were determined for compounds defined as "hits." The Fluo4 cell-based fluorescence assay was used to determine the intracellular Ca²⁺ concentration in the presence of varying drug concentration. Concentrations tested were 40 µM, 20 µM, 10 µM, 5 µM, 2.5 µM, 1.25 µM, and 0.625 µM. Compounds were tested in triplicate at all concentrations. Standard software was used to fit IC$_{50}$ curves.

Additionally or alternatively, efficacy can be represented as % inhibition in the presence (of a given concentration of compound) versus the absence of compound or in comparison to a control compound. For example, efficacy can be represented as % inhibition of ion flux in the presence versus the absence of compound.

Example 2: Patch Clamp Experiments

Patch clamp experiments permit the detection of currents through the TRPC5 channel in the cell line described above. In normal whole-cell patch clamp recordings, a glass electrode is brought into contact with a single cell and a high-resistance (gigaohm) seal is established with the cell membrane. The membrane is then ruptured to achieve the whole-cell configuration, permitting control of the voltage of the cell membrane and measurement of currents flowing across the membrane using the amplifier attached to the electrode and resulting in the replacement of cytoplasm with the pipette solution. A perfusion system permits control of the extracellular solution, including the addition of blockers and activators of the current. The current can be activated by including 1.4 µM free Ca²⁺ in the pipette (intracellular) solution, and 80 µM LaCl$_3$ in the extracellular solution.

TRPC5 cells were induced 20-48 hours, removed from growth plates, and replated at low density (to attain good single-cell physical separation) on glass coverslips for measurement. In some cases, cells were grown in low density overnight on glass coverslips. Patch clamp recordings were made in the whole-cell mode with a holding potential of −40 mV. Every 5 seconds, a voltage ramp was applied from −120 to +100 mV, 400 ms in duration. Currents elicited were quantified at −80 mV and +80 mV. The internal solution consisted of 140 mM cesium aspartate, 10 mM HEDTA, 2 mM CaCl$_2$, 2.27 mM MgCl$_2$ and 10 mM REYES, pH 7.2, with 1,400 nM calculated free Ca²⁺. The external solution consisted of 150 mM NaCl, 4.5 mM KCl, 3 mM MgCl$_2$, 10 mM HEPES, 10 mM glutamine, 1 mM EGTA, pH 7.4. Upon addition of LaCl$_3$, TRPC5 current was induced only in TRPC5-expressing cells and not in parental HEK293 TREx cells. Removal of the LaCl$_3$ stimulus causes most of the current to go away. Potential blockers were tested for ability to block both inward and outward currents in the continued presence of LaCl$_3$.

IC$_{50}$ of compounds was estimated by testing each compound at 5 µM and 500 nM. When 5 µM compound showed no block, IC$_{50}$ was estimated as >10 µM. When 5 µM compound showed 50% or less block, a rough estimate of IC$_{50}$ in the range of 5-10 µM could be made. IC$_{50}$ for compounds between 500 nM and 5 µM was similarly estimated. Compounds blocking 50% or more at 500 nM are retested at multiple concentrations, and the % block at each is fitted by standard equations to determine IC$_{50}$ accurately using a 5-6 point concentration/response experiment.

INCORPORATION BY REFERENCE

All publications and patents mentioned herein, are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A method of treating anxiety in a subject, the method comprising administering an effective amount of a compound of Formula (I) to the subject:

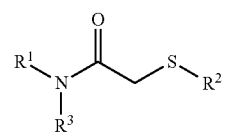

Formula (I)

or a pharmaceutically acceptable salt thereof, wherein:

R¹ is aryl or heteroaryl, optionally substituted with 1-5 R⁴;

R² is 5-membered heteroaryl or a fused heteroaryl, optionally substituted with 1-5 R⁵;

R³ is H, C$_1$-C$_6$ alkyl, arylalkyl, or a nitrogen protecting group;

each R⁴ is independently C$_1$-C$_6$ alkyl, C$_1$-C$_6$ haloalkyl, —C(O)R⁶, —C(O)OR⁶, —OR⁶, or —C(O)NR⁷R⁸; or 2 R⁴, taken together with the carbon atom to which they are attached, form a 4-6 membered ring;

each R⁵ is independently C$_1$-C$_6$ alkyl, cyclyl, heterocyclyl, aryl, or heteroaryl;

each R⁶ is independently H, C$_1$-C$_6$ alkyl, or C$_1$-C$_6$ haloalkyl; and each R⁷ and R⁸ is independently H or C$_1$-C$_6$ alkyl to thereby treat the subject.

2. The method of claim 1, wherein R¹ is aryl optionally substituted with 1-5 R⁴.

3. The method of claim 2, wherein R¹ is phenyl substituted by 1-2 R⁴.

4. The method of claim 3, wherein R⁴ is C$_1$-C$_6$ haloalkyl.

5. The compound of claim 4, wherein R⁴ is CF$_3$.

6. The method of claim 2, wherein R¹ is

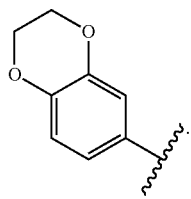 [SMILES: *c1ccc2c(c1)OCCO2]

7. The method of claim 1, wherein R¹ is heteroaryl substituted with 1-5 R⁴.

8. The method of claim 7, wherein R¹ is

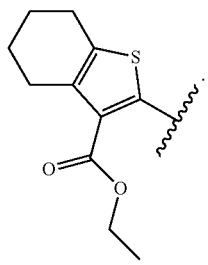 [SMILES: *c1sc2c(c1C(=O)OCC)CCCC2]

9. The method of claim 1, wherein R² is a 5-membered heteroaryl optionally substituted with 1-5 R⁵.

10. The method of claim 9, wherein R² is tetrazolyl.

11. The method of claim 10, wherein R² is

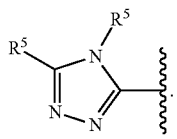

12. The method of claim 11, wherein each R⁵ is independently C₁-C₆ alkyl or heteroaryl.

13. The method of claim 12, wherein R² is

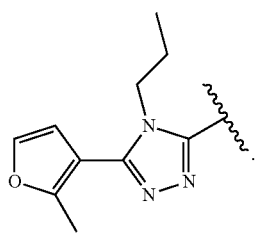 [SMILES: *c1nnc(-c2ccoc2C)n1CCC]

14. The method of claim 1, wherein R² is a fused heteroaryl.

15. The method of claim 14, wherein R² is

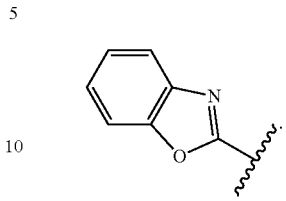

16. The method of claim 1, wherein R³ is H.

17. The method of any one of claims 1-16, wherein the compound is selected from the group consisting of:

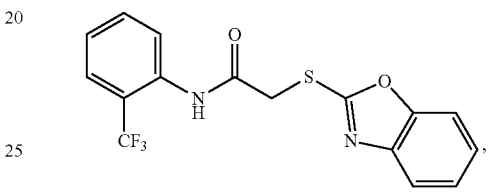

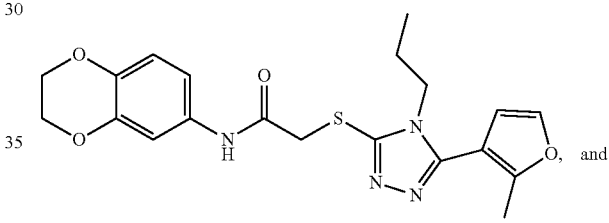

and

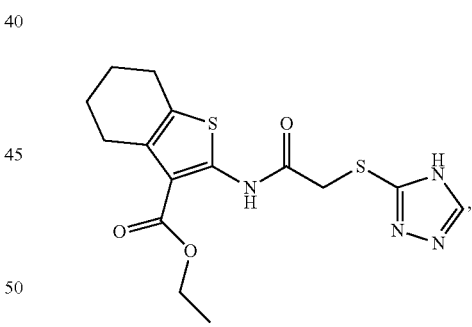

or a pharmaceutically acceptable salt thereof.

* * * * *